US008444267B2

(12) United States Patent
Weeber et al.

(10) Patent No.: US 8,444,267 B2
(45) Date of Patent: May 21, 2013

(54) OPHTHALMIC LENS, SYSTEMS AND METHODS WITH ANGULAR VARYING PHASE DELAY

(75) Inventors: Hendrik A. Weeber, Groningen (NL); Scott J. Catlin, Orange, CA (US)

(73) Assignee: AMO Groningen B.V., Groningen (NL)

( * ) Notice: Subject to any disclaimer, the term of this patent is extended or adjusted under 35 U.S.C. 154(b) by 64 days.

(21) Appl. No.: 12/971,889

(22) Filed: Dec. 17, 2010

(65) Prior Publication Data
US 2011/0317124 A1   Dec. 29, 2011

Related U.S. Application Data

(60) Provisional application No. 61/288,255, filed on Dec. 18, 2009.

(51) Int. Cl.
*G02C 7/02* (2006.01)
(52) U.S. Cl.
USPC .................................. 351/159.44; 351/159.35
(58) Field of Classification Search
USPC ............. 351/159.01, 159.02, 159.11–159.13, 351/159.15, 159.26, 159.35, 159.44, 159.74–159.77; 623/5.11–5.16, 6.11–6.62
See application file for complete search history.

(56) References Cited

U.S. PATENT DOCUMENTS

| | | | |
|---|---|---|---|
| 3,367,734 A | 2/1968 | Bystricky et al. | |
| 4,637,697 A | 1/1987 | Freeman | |
| 4,642,112 A | 2/1987 | Freeman | |
| 4,655,565 A | 4/1987 | Freeman | |
| 4,778,462 A | 10/1988 | Grendahl | |
| 4,795,462 A | 1/1989 | Grendahl | |
| 4,798,608 A | 1/1989 | Grendahl | |
| 4,798,609 A | 1/1989 | Grendahl | |
| 4,932,970 A | 6/1990 | Portney | |
| 4,995,714 A | 2/1991 | Cohen | |
| 4,995,715 A | 2/1991 | Cohen | |
| 5,016,977 A | 5/1991 | Baude et al. | |
| 5,056,908 A | 10/1991 | Cohen | |
| 5,066,301 A | 11/1991 | Wiley | |
| 5,089,023 A | 2/1992 | Swanson | |
| 5,096,285 A | 3/1992 | Silberman | |
| 5,114,220 A | 5/1992 | Baude et al. | |
| 5,117,306 A | 5/1992 | Cohen | |
| 5,120,120 A | 6/1992 | Cohen | |
| 5,121,979 A | 6/1992 | Cohen | |

(Continued)

FOREIGN PATENT DOCUMENTS

| | | |
|---|---|---|
| EP | 343067 A1 | 11/1989 |
| EP | 457553 A2 | 11/1991 |

(Continued)

OTHER PUBLICATIONS

International Search Report and Written Opinion for Application No. PCT/IB2011/001067, mailed Sep. 13, 2011, 13 pages.

(Continued)

*Primary Examiner* — Darryl J Collins
(74) *Attorney, Agent, or Firm* — AMO Groningen B.V.

(57) ABSTRACT

An ophthalmic lens, such as an intraocular lens (IOL), a phakic IOL or a corneal implant, and a system and method relating to same, having coupled thereto one or more rotationally asymmetric and/or non-continuous diffractive zones, such as for providing improved multifocal vision correction.

14 Claims, 6 Drawing Sheets

U.S. PATENT DOCUMENTS

| | | | |
|---|---|---|---|
| 5,121,980 A | 6/1992 | Cohen | |
| 5,144,483 A | 9/1992 | Cohen | |
| 5,225,858 A | 7/1993 | Portney | |
| 5,229,797 A | 7/1993 | Futhey et al. | |
| 5,408,281 A * | 4/1995 | Zhang | 351/159.41 |
| 5,652,638 A | 7/1997 | Roffman et al. | |
| 5,699,142 A | 12/1997 | Lee et al. | |
| 5,748,282 A | 5/1998 | Freeman | |
| 5,760,871 A | 6/1998 | Kosoburd et al. | |
| 5,796,462 A | 8/1998 | Roffman et al. | |
| 5,968,094 A | 10/1999 | Werblin et al. | |
| 6,126,283 A | 10/2000 | Wen et al. | |
| 6,126,286 A | 10/2000 | Portney | |
| 6,142,625 A | 11/2000 | Sawano et al. | |
| 6,210,005 B1 | 4/2001 | Portney | |
| 6,338,559 B1 | 1/2002 | Williams et al. | |
| 6,457,826 B1 | 10/2002 | Lett | |
| 6,464,355 B1 | 10/2002 | Gil | |
| 6,474,814 B1 | 11/2002 | Griffin | |
| 6,488,708 B2 | 12/2002 | Sarfarazi | |
| 6,491,721 B2 | 12/2002 | Freeman et al. | |
| 6,527,389 B2 | 3/2003 | Portney | |
| 6,533,416 B1 | 3/2003 | Fermigier et al. | |
| 6,536,899 B1 | 3/2003 | Fiala | |
| 6,537,317 B1 | 3/2003 | Steinert et al. | |
| 6,547,822 B1 | 4/2003 | Lang | |
| 6,554,859 B1 | 4/2003 | Lang et al. | |
| 6,557,992 B1 | 5/2003 | Dwyer et al. | |
| 6,609,793 B2 | 8/2003 | Norrby et al. | |
| 6,705,729 B2 | 3/2004 | Piers et al. | |
| 6,808,262 B2 | 10/2004 | Chapoy et al. | |
| 6,830,332 B2 | 12/2004 | Piers et al. | |
| 6,846,326 B2 | 1/2005 | Zadno-Azizi et al. | |
| 6,851,803 B2 | 2/2005 | Wooley et al. | |
| 6,923,539 B2 | 8/2005 | Simpson et al. | |
| 6,923,540 B2 | 8/2005 | Ye et al. | |
| 6,986,578 B2 | 1/2006 | Jones | |
| 7,036,931 B2 | 5/2006 | Lindacher et al. | |
| 7,048,760 B2 | 5/2006 | Cumming | |
| 7,061,693 B2 | 6/2006 | Zalevsky | |
| 7,073,906 B1 | 7/2006 | Portney | |
| 7,137,702 B2 | 11/2006 | Piers et al. | |
| 7,156,516 B2 | 1/2007 | Morris et al. | |
| 7,188,949 B2 | 3/2007 | Bandhauer et al. | |
| 7,287,852 B2 | 10/2007 | Fiala | |
| 7,293,873 B2 | 11/2007 | Dai et al. | |
| 7,365,917 B2 | 4/2008 | Zalevsky | |
| 7,377,640 B2 | 5/2008 | Piers et al. | |
| 7,441,894 B2 | 10/2008 | Zhang et al. | |
| 7,475,986 B2 | 1/2009 | Dai et al. | |
| 7,615,073 B2 | 11/2009 | Deacon et al. | |
| 7,871,162 B2 | 1/2011 | Weeber | |
| 2002/0118337 A1 | 8/2002 | Perrott et al. | |
| 2003/0076478 A1 | 4/2003 | Cox | |
| 2003/0171808 A1 | 9/2003 | Phillips | |
| 2004/0021824 A1 | 2/2004 | Ye et al. | |
| 2004/0085515 A1 | 5/2004 | Roffman et al. | |
| 2004/0106992 A1 | 6/2004 | Lang et al. | |
| 2004/0111153 A1 | 6/2004 | Woods et al. | |
| 2004/0150789 A1 | 8/2004 | Jones | |
| 2004/0156014 A1 | 8/2004 | Piers et al. | |
| 2004/0230299 A1 | 11/2004 | Simpson et al. | |
| 2005/0096226 A1 | 5/2005 | Stock et al. | |
| 2005/0128432 A1 | 6/2005 | Altmann | |
| 2005/0203619 A1 | 9/2005 | Altmann | |
| 2005/0267575 A1 | 12/2005 | Nguyen et al. | |
| 2006/0009816 A1 | 1/2006 | Fang et al. | |
| 2006/0030938 A1 | 2/2006 | Altmann | |
| 2006/0034003 A1 | 2/2006 | Zalevsky | |
| 2006/0055883 A1 | 3/2006 | Morris et al. | |
| 2006/0066808 A1 | 3/2006 | Blum et al. | |
| 2006/0098162 A1 | 5/2006 | Bandhauer et al. | |
| 2006/0098163 A1 | 5/2006 | Bandhauer et al. | |
| 2006/0109421 A1 | 5/2006 | Ye et al. | |
| 2006/0116763 A1 | 6/2006 | Simpson | |
| 2006/0116764 A1 | 6/2006 | Simpson | |
| 2006/0176572 A1 | 8/2006 | Fiala | |
| 2006/0238702 A1 | 10/2006 | Glick et al. | |
| 2006/0244904 A1 | 11/2006 | Hong et al. | |
| 2007/0052920 A1 | 3/2007 | Stewart et al. | |
| 2007/0129803 A1 | 6/2007 | Cumming et al. | |
| 2007/0171362 A1 | 7/2007 | Simpson et al. | |
| 2007/0182924 A1 | 8/2007 | Hong et al. | |
| 2008/0030677 A1 | 2/2008 | Simpson | |
| 2008/0161913 A1 | 7/2008 | Brady et al. | |
| 2008/0161914 A1 | 7/2008 | Brady et al. | |
| 2009/0062911 A1 | 3/2009 | Bogaert | |
| 2009/0164008 A1 | 6/2009 | Hong et al. | |
| 2009/0187242 A1 | 7/2009 | Weeber et al. | |
| 2009/0210054 A1 | 8/2009 | Weeber et al. | |
| 2009/0234448 A1 | 9/2009 | Weeber et al. | |
| 2009/0268155 A1 | 10/2009 | Weeber | |
| 2009/0268158 A1 | 10/2009 | Weeber | |
| 2009/0295295 A1 | 12/2009 | Shannon et al. | |
| 2009/0323020 A1 | 12/2009 | Zhao et al. | |
| 2010/0016961 A1 | 1/2010 | Hong et al. | |
| 2010/0161048 A1 | 6/2010 | Schaper, Jr. | |

FOREIGN PATENT DOCUMENTS

| | | |
|---|---|---|
| EP | 681198 A1 | 11/1995 |
| EP | 0926531 A1 | 6/1999 |
| EP | 949529 A2 | 10/1999 |
| EP | 1424049 A1 | 6/2004 |
| EP | 1310267 B1 | 1/2008 |
| EP | 1424049 B1 | 6/2009 |
| WO | WO9222264 A1 | 12/1992 |
| WO | WO9303409 A1 | 2/1993 |
| WO | WO0019906 A1 | 4/2000 |
| WO | WO0163344 A1 | 8/2001 |
| WO | WO0182839 A1 | 11/2001 |
| WO | WO0189424 A1 | 11/2001 |
| WO | WO0221194 A2 | 3/2002 |
| WO | WO03009053 A1 | 1/2003 |
| WO | WO2004034129 A1 | 4/2004 |
| WO | WO2004090611 A2 | 10/2004 |
| WO | WO2004096014 A2 | 11/2004 |
| WO | WO2005019906 A1 | 3/2005 |
| WO | WO2006025726 A1 | 3/2006 |
| WO | WO2006047698 A1 | 5/2006 |
| WO | WO2006060477 A2 | 6/2006 |
| WO | WO2006060480 A2 | 6/2006 |
| WO | WO2007092948 A1 | 8/2007 |
| WO | WO2007133384 A2 | 11/2007 |
| WO | WO2008045847 A2 | 4/2008 |
| WO | WO2009076670 A1 | 6/2009 |

OTHER PUBLICATIONS

Piers P.A., et al., "Eye Models for the Prediction of Contrast Vision in Patients with New Intraocular Lens Designs," Optics Letters, 2004, vol. 29 (7), pp. 733-735.

Terwee T., et al., "Visualization of the Retinal Image in an Eye Model With Spherical and Aspheric, Diffractive, and Refractive Multifocal Intraocular Lenses," Journal of Refractive Surgery, 2008, vol. 24 (3), pp. 223-232.

Alfonso J.F., et al., "Prospective Study of the Acri.LISA bifocal Intraocular Lens,".

Journal of Cataract Refractive Surgery, 2007, vol. 33 (11), pp. 1930-1935.

Canovas C., et al., "Hybrid Adaptive-Optics Visual Simulator," Optical Letters, 2010, vol. 35 (2), pp. 196-198.

Cohen, Allen L., "Practical design of a bifocal hologram contact lens or intraocular lens," Applied Optics, 1992, 31 (19), 3750-3754.

Co-pending U.S. Appl. No. 12/771,550.

Diffractive Lenses for Extended Depth of Focus and Presbyopic Correction. Presentation from Wavefront Congress held on Feb. 15, 2008, Rochester, New York.

Doskolovich L.L., et al., "Special Diffractive Lenses," SPIE, 1992, vol. 1780, pp. 393-402.

International Search Report for Application No. PCT/EP2008/061235, mailed on Mar. 5, 2009, 4 pages.

International Search Report for Application No. PCT/EP2009/051783, mailed on Apr. 28, 2009, 3 pages.

International Search Report for Application No. PCT/US09/042449, mailed on Nov. 5, 2009, 5 pages.

International Search Report for Application No. PCT/US2010/038167, mailed on Sep. 27, 2010, 2 pages.

Liou H.L., et al., "Anatomically Accurate, Finite Model Eye for Optical Modeling," Journal of Optical Society of America, 1997, vol. 14 (8), pp. 1684-1695.

Marsack J.D., et al., "Metrics of Optical Quality Derived From Wave Aberrations Predict Visual Performance," Journal of Vision, 2004, vol. 4 (4), pp. 322-328.

Monsoriu J.A., et al., "Devil's Lenses," Optics Express, 2007, vol. 15 (21), pp. 13858-13864.

Norrby S., et al., "Model Eyes for Evaluation of Intraocular Lenses," Applied Optics, 2007, vol. 46 (26), pp. 6595-6605.

Piers P.A., et al., "Theoretical Comparison of Aberration-Correcting Customized and Aspheric Intraocular Lenses," Journal of Refractive Surgery, 2007, vol. 23 (4), pp. 374-384.

Siedlecki D., et al., "Radial Gradient index Intraocular Lens: a Theoretical Model," Journal of Modern Optics, 2008, vol. 55 (4-5), pp. 639-647.

Van Meeteren A., "Calculations on the Optical Modulation Transfer Function of the Human Eye for White Light," Optica Acta, 1974, vol. 21 (5), pp. 395-412.

Vanden Berg T.J., "Analysis of Intraocular Straylight Especially in Relation to Age," Optometry and Vision Science, 1995, vol. 72 (2), pp. 52-59.

Villegas E.A., et al., "Correlation between Optical and Psychophy, Sical Parameters as a Function of Defocus," Optometry and Vision Science, 2002, vol. 79 (1), pp. 60-67.

International Search Report for Application No. PCT/US2010/061081, mailed on Apr. 6, 2011, 2 pages.

International Search Report for Application No. PCT/IB2006/005590, mailed on Sep. 30, 2009, 3 pages.

International Search Report for Application No. PCT/US08/073999, mailed on Dec. 3, 2008, 3 pages.

U.S. Appl. No. 12/429,155, filed Apr. 23, 2009.

U.S. Appl. No. 11/618,325, filed Dec. 29, 2006 (Brady et al).

U.S. Appl. No. 11/618,411, filed Dec. 29, 2006(Bradyetai).

U.S. Appl. No. 12/109,251, filed Apr. 24, 2008.

Co-pending U.S. Appl. No. 12/503,267, filed Jul. 15, 2009.

\* cited by examiner

OPHTHALMIC LENS, SYSTEMS AND METHODS WITH ANGULAR VARYING PHASE DELAY

CROSS-REFERENCES TO RELATED APPLICATIONS

This application claims priority under 35 U.S.C §119(e) to provisional application No. 61/288,255 filed on Dec. 18, 2009, the entire contents of which are incorporated herein by reference. This application is related to the following applications which were filed concurrently herewith: Single Microstructure Lens, Systems And Methods, U.S. patent application Ser. No. 12/971,506, filed on Dec. 17, 2010; Limited Echelette Lens, Systems And Methods, U.S. patent application Ser. No. 12/971,607, filed on Dec. 17, 2010; and Ophthalmic Lens, Systems And Methods Having At Least One Rotationally Asymmetric Diffractive Structure, U.S. Patent Application No. 61/424,433, filed on Dec. 17, 2010. The entire contents of these three applications are also incorporated herein by reference. This application is also related to the following U.S. Patent Application No. 61/047,699 and Ser. No. 12/109,251, both filed on Apr. 24, 2008; Ser. No. 12/429,155 filed on Apr. 23, 2009; Ser. No. 12/372,573 filed on Feb. 17, 2009; Ser. No. 12/197,249 filed on Aug. 23, 2008; Ser. No. 12/120,201 filed on Apr. 13, 2008, and Ser. No. 12/771,550 filed on Apr. 30, 2010. Full Paris Convention priority is hereby expressly reserved.

BACKGROUND OF THE INVENTION

1. Field of the Invention

This invention relates generally to an ophthalmic lens, and more specifically to an ophthalmic lens having coupled thereto or integrated thereon one or more rotationally asymmetric and/or non-continuous diffractive zones for varying phase delay in order to improve vision at a range of distances, as well as systems and methods relating to same.

2. Description of the Related Art

Surgery on the human eye has become commonplace in recent years. Many patients pursue eye surgery as an elective procedure, such as to avoid the use of contacts or glasses. Other patients pursue surgery to correct an adverse condition in the eye. Such adverse conditions may include, for example, cataracts or presbyopia, as well as other conditions known to those skilled in the art.

The anatomy and physiology of the human eye is well understood. Generally speaking, the structure of the human eye includes an outer layer formed of two parts, namely the cornea and the sclera. The middle layer of the eye includes the iris, the choroid, and the ciliary body. The inner layer of the eye includes the retina. The eye also includes, physically associated with the middle layer, a crystalline lens that is contained within an elastic capsule, also referred to as the lens capsule, or capsular bag. Image formation in the eye occurs by entry of image-forming light to the eye through the cornea, and refraction by the cornea and the crystalline lens to focus the image-forming light on the retina. The retina provides the light sensitive tissue of the eye.

Ophthalmic lenses, such as intraocular lenses (IOLs), phakic IOLs and corneal implants may be used to enhance or correct vision, such as to correct for the aforementioned adverse conditions, including aberrations or inadequacies that adversely affect the performance of the referenced structures of the eye. For example, IOLs are routinely used to replace the crystalline lens of an eye that is removed during cataract surgery.

Ophthalmic lenses, such as IOLs, may be monofocal, multifocal, or may include monofocal and multifocal portions. More particularly, a monofocal IOL portion may provide a single focal point, whereas a multifocal IOL portion may provide multiple focal points, such as for correction of vision at different distances. For example, a bifocal IOL may provide two different focal points, typically for near and distant vision.

A diffractive bifocal IOL may divide incident light into two diffractive orders to provide the aforementioned near and distant bifocal vision. In such lenses, the optic area is generally divided into a plurality of echelettes that are offset parallel to the optical axis by predetermined diffractive step heights in order to provide a specific phase relationship.

A phase "plate" is typically comprised of a plurality of echelettes in which the optical height of the steps causes a phase delay. For example, a step height of one-half times the design wavelength results in approximately 80% of the light at the design wavelength being evenly split between zeroeth and first diffraction orders. This phase plate configuration may be used to produce a bifocal lens in which the zeroeth diffraction order produces a first focal point for distant vision, and the first diffraction order produces a second focal point corresponding to near or intermediate vision. A step height equal to the design wavelength results in a monofocal diffractive IOL that may be used to correct for chromatic aberration.

A first particular problem associated with diffractive multifocal/bifocal IOLs is dysphotopsia, i.e. halos and glare. Halos arise when light from the unused focal image creates an out-of-focus image that is superimposed on the used focal image. For example, if light from a distant point source is imaged onto the retina by the distant focus of a bifocal IOL, the near focus of the IOL will simultaneously superimpose a defocused image on top of the image formed by the distant focus. This defocused image may manifest itself in the form of a ring of light surrounding the in-focus image, referred to as a halo. A second problem frequently associated with diffractive multifocal/bifocal IOLs is reduced contrast vision. These difficulties arise, at least in part, due to the symmetric, and/or the concentric, nature of the aforementioned diffractive echelettes of the IOL.

Thus, a need exists for a lens, system and method that improves the performance of multifocal lenses, and particularly of multifocal ophthalmic lenses.

SUMMARY OF THE INVENTION

The present invention includes ophthalmic lenses such as spectacles, contact lenses, corneal inlays or onlays, or intraocular lenses (IOLs) including, for example, phakic IOLs and piggyback IOLs having coupled thereto or integrated thereon at least one rotationally asymmetric diffractive structure and a system and method relating to same. The lens of the present invention may include one or more surface regions having a refractive optical power and/or a diffractive optical power that together enhance vision.

More particularly, in embodiments of the present invention, an ophthalmic lens may include one or more rotationally asymmetric and/or non-continuous diffractive zones, such as for providing improved multifocal vision.

A multifocal ophthalmic lens, system and method in accordance with the present invention may include an optic having an anterior surface, a posterior surface, and an optical axis, wherein the optic includes at least one refractive region associated with at least one of the anterior surface and the posterior surface, and at least one diffractive region comprising a plurality of diffractive echelettes coupled with at least a portion of the at least one refractive region and having a rotational asymmetry with respect to the optical axis. The phase plate may have at least two diffractive orders with associated diffractive optical powers configured for forming, in conjunction with the coupled portion of the at least one refractive region, at least a first focus and a second focus.

The aforementioned first focus may be configured to provide distant vision, and the second focus may be configured to provide near vision. The refractive region may comprise approximately half of the optic while the diffractive region may comprise the other half of the optic, by way of non-limiting example. The plurality of echelettes may comprise a step height as between adjacent ones of the plurality of echelettes.

A multifocal ophthalmic lens, system and method in accordance with the present invention may further include at least one or more rotationally asymmetric and/or non-continuous zone wherein each respective step height in the zone may vary tangentially as a function of the rotational angle or vary around a particular circumference along the optic.

Systems and methods in accordance with the present invention may include any manner of providing an ophthalmic lens having one or more rotationally asymmetric structures. Such systems and method may include, and/or may be executed by, for example, hardware, software, and computing systems and processes.

Thus, the present invention provides a lens apparatus, system and method that improve the performance of diffractive lenses, and particularly of multifocal and/or toric ophthalmic lenses, in ophthalmic applications.

BRIEF DESCRIPTION OF THE DRAWINGS

Understanding of the present invention will be facilitated by consideration of the following detailed description of the preferred embodiments of the present invention taken in conjunction with the accompanying drawings, in which like numerals refer to like parts, and in which.

Figure 1:
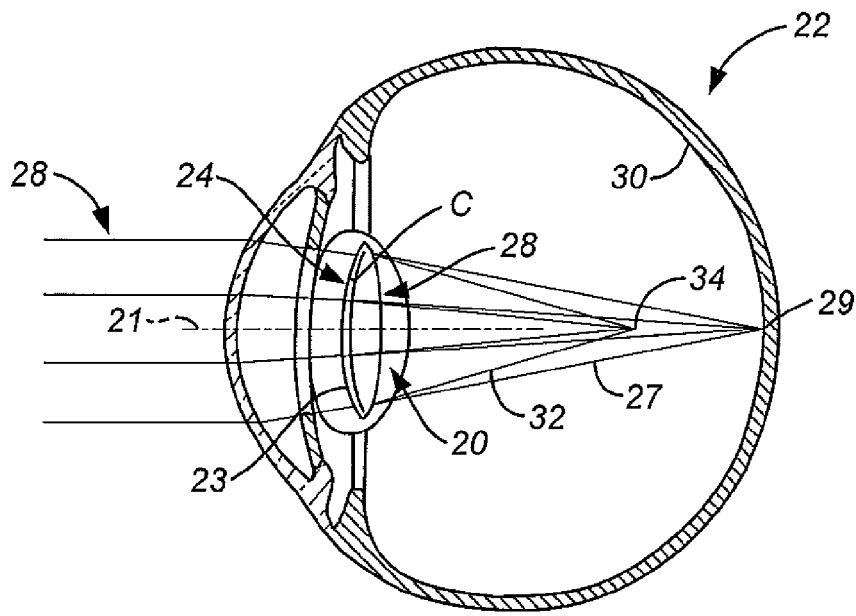
FIG. 1 is a schematic illustration of an eye including a prior art intraocular lens.

For illustration purposes, the profile geometries shown in certain aforementioned figures were not drawn exactly to scale. The heights of the profiles shown in the figures are generally on the order of 0(zero) μmeters to about 8.0 μmeters although the heights may vary depending on factors such as the amount of correction needed by the patient, the refractive index of the lens material and surrounding medium, and the desired phase shift/delay.

DETAILED DESCRIPTION

It is to be understood that the figures and descriptions of the present invention have been simplified to illustrate elements that are relevant for a clear understanding of the present invention, while eliminating, for the purpose of clarity, many other elements found in typical lenses, lens systems and methods. Those of ordinary skill in the pertinent arts may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the pertinent arts.

The present invention is directed to an ophthalmic lens such as, for example, spectacles, contact lenses, corneal inlays or onlays, or intraocular lenses (IOLs) including, for example, phakic IOLs and piggyback IOLs, having thereupon at least one rotationally asymmetric diffractive structure and a system and method relating to same. The lens of the present invention may include one or more surface regions having a refractive optical power and a diffractive optical power that together enhance vision. The terms "power" or "optical power" are used herein to indicate the ability of a lens, an optic, an optical surface, or at least a portion of an optical surface, to redirect incident light for the purpose of forming a real or virtual focal point. Optical power may result from reflection, refraction, diffraction, or some combination thereof and is generally expressed in units of Diopters. One of skill in the art will appreciate that the optical power of a surface, lens, or optic is generally equal to the reciprocal of the focal length of the surface, lens, or optic, when the focal length is expressed in units of meters. Further, as used herein, the term "refractive optical power" or "refractive power" includes optical power produced by the refraction of light as it interacts with a surface, lens, or optic, and the term "diffractive optical power" or "diffractive power" includes optical power resulting from interference of non-refractive light, and may or may not be related to the diffraction of light as it interacts with a surface, lens, or optic.

More particularly, in embodiments of the present invention, an ophthalmic lens may include one or more rotationally asymmetric and/or non-continuous diffractive zones, such as for providing improved multifocal vision correction. The embodiments of the corrective lens, system and method of the present invention thus provide improved performance after implantation, such as by at least reducing halos and improving contrast vision. The present invention is directed to ophthalmic lenses mentioned herein, as well as, corneal reshaping procedures and combinations of the foregoing.

FIG. 1 illustrates an IOL 20 having an optical axis 21 disposed in an eye 22. The IOL 20 may comprise a phase plate 23 having at least one diffractive structure Phase plate 23 may be disposed on an anterior surface 24 having a base curvature C, and may be illuminated by incident light 26 from a distant object that enters eye 22 in the form of collimated light. A first portion 27 of incident light 26 may be substantially unaffected by phase plate 23 and is focused by anterior surface 24 and a posterior surface 28, through refraction, to produce a first focus 29 approximately located on a retina 30 of eye 22 for providing distant vision. A second portion 32 of incident light 26 may be diffracted by phase plate 23 to form a second focus 34. The net optical power of anterior surface 24 for forming the second focus 34 is generally considered to be a combination of the refractive optical power of the anterior surface 24 due to the base curvature C, and the diffractive optical power of phase plate 23.

The term "near vision," as used herein, refers to vision provided by at least a portion of a lens, such as IOL 20, wherein objects relatively close to the subject are substantially in focus on the retina of the subject eye. The term "near vision' generally corresponds to vision provided when objects are at a distance from the subject eye of between about 1 to 2 feet. The term "distant vision," as used herein, refers to vision provided by at least a portion of a lens, wherein objects relatively far from the subject are substantially in focus on the retina of the eye. The term "distant vision" generally corresponds to vision provided when objects are at a distance of at least about 6 feet or greater. The term "intermediate vision," as used herein, refers to vision provided by at least a portion of a lens, wherein objects at an intermediate distance from the subject are substantially in focus on the retina of the eye. Intermediate vision generally corresponds to vision provided when objects are at a distance of about 2 feet to about 5 feet from the subject eye.

The ophthalmic lens, system and method of the present invention preferably provide an improved correction of at least one of near, intermediate or distant vision, and/or of at least one aberration or subjective performance inadequacy, in accordance with the aforementioned presence of at least one rotationally asymmetric diffractive structure. For example, an ophthalmic lens having multiple rotationally asymmetric echelettes may provide improved multifocal vision correction by reducing halos and improving contrast vision, as discussed immediately below.

Figure 2:
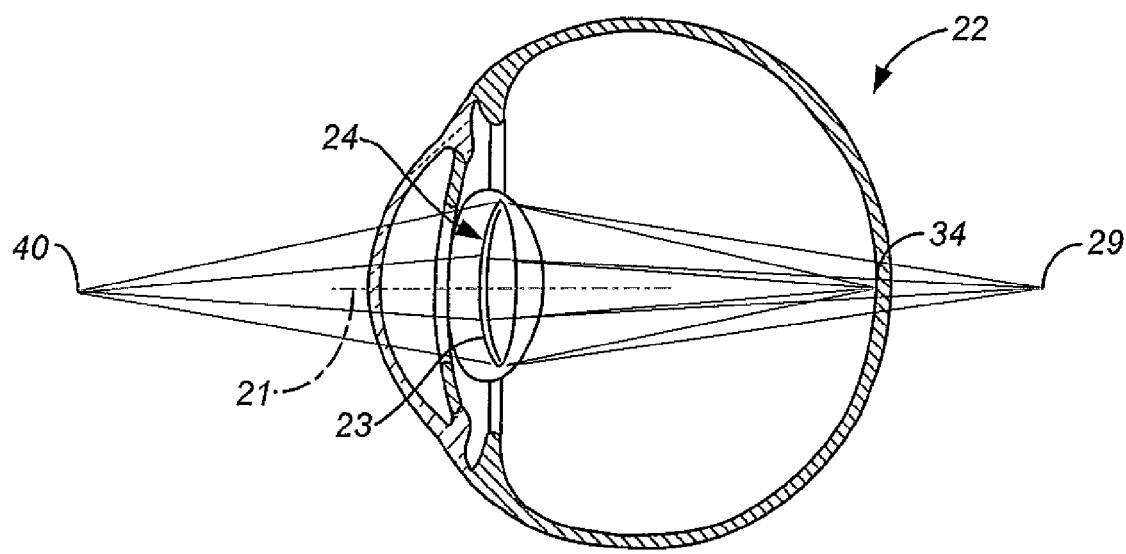
FIG. 2 is a schematic illustration of an eye including a prior art intraocular lens.

FIG. 2 illustrates the performance of a bifocal IOL 20 for a near object 40 located relatively close to eye 22. Under these conditions, distant and near foci 29, 34 are disposed such that near focus 34 is approximately located on retina 30, and distant focus 29 is located behind retina 30. Therefore, IOL 20 may function as a bifocal lens that provides a patient with both near and distant vision in a manner that approximates the accommodative ability of the natural lens of eye 22 when that lens is lost due to presbyopia and/or removal, by way of example.

Phase plate 23 of a typical bifocal IOL 20 is generally comprised of a plurality of echelettes, having a particular offset or step height along the optical axis 21. As used herein, the term "zone" or "angular section" may be used to identify portions of an optic which are distinguishable from an adjacent portion of an optic based on optical properties of the zone. For example, adjacent zones may be refractive and diffractive. Two adjacent zones may also be diffractive with different phase discontinuities or stepheights. Additionally, one zone may have a constantly varying phase continuity wherein the stepheight varies tangentially as a function of the rotational angle. Such a zone, may for example, have a stepheight that transitions from the stepheight of one adjacent zone and increases/decreases until it reaches the stepheight of the other adjacent zone, as detailed below.

The bifocal characteristics of a typical IOL 20 may be realized by selecting the echelette stepheight such that rays to either side of the step experience a difference in optical path length of, for example, $\lambda/2$, where $\lambda$ is a design wavelength. Alternatively, a typical IOL 20 may be in the form of a monofocal IOL in which the step height is such that rays to either side of the step experience a difference in optical path length of $\lambda$. The benefits of such a monofocal diffractive include chromatic aberration correction. Of course, those skilled in the art will appreciate that other multiples of $\lambda$ are also frequently employed in the pertinent arts to vary the optical path length.

Figure 3:
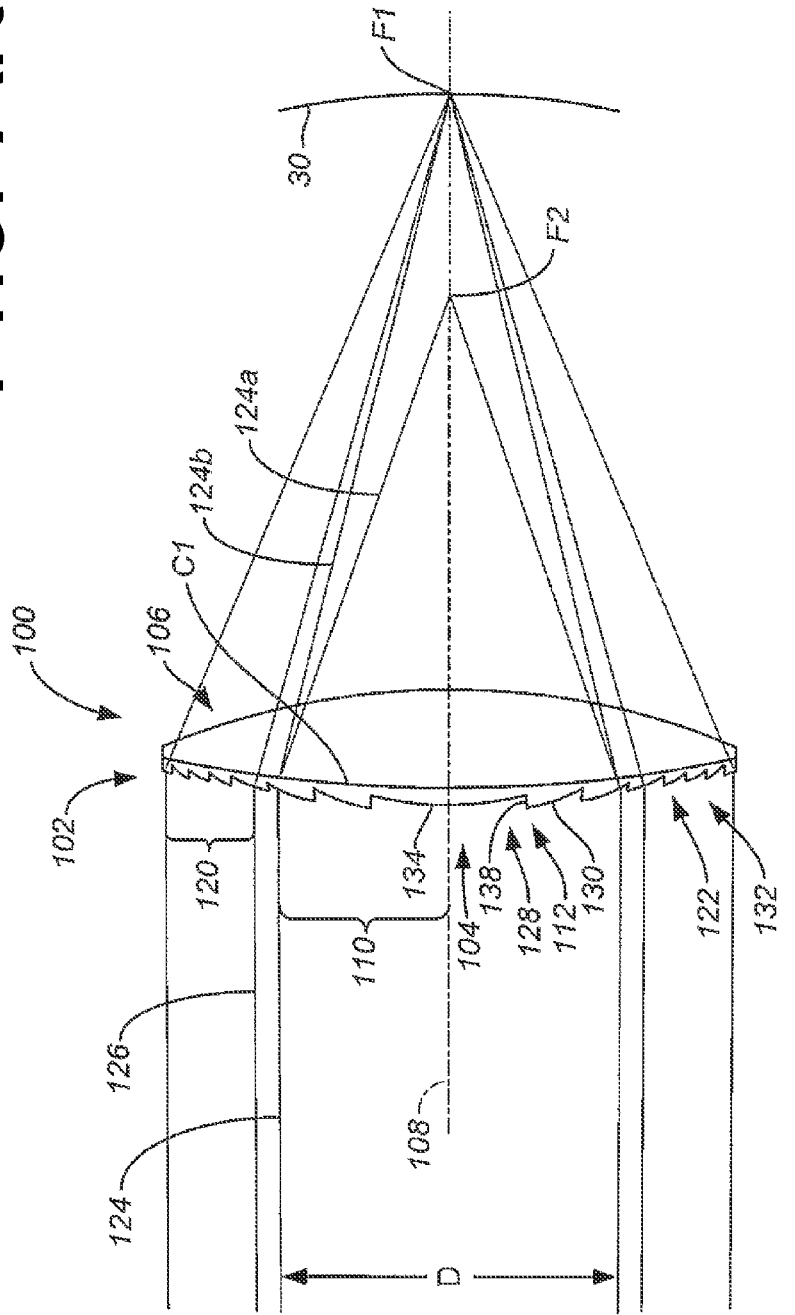
FIG. 3 is a schematic illustration of a prior art ophthalmic lens.

Referring now to FIG. 3, an ophthalmic lens 100 preferably includes optic 102. Optic 102 has an anterior surface 104, a posterior surface 106, and an optical axis 108. The optic 102 may comprise a first region 110 having an optical power and comprising a multifocal phase plate 112 for producing a first focal point F1 (zeroeth order) and a second focal point F2 (first order). By way of example, input light ray 124 may be split into two focused light rays 124a and 124b, directed to the first focus F1 and the second focus F2, respectively. In certain embodiments, phase plate 112 may be disposed on the anterior surface 104. Alternatively, the phase plate 112 may be disposed on the posterior surface 106. As understood to those skilled in the art, the diffractive structure may be coupled to the optic, or integrated thereon.

The diffraction orders (and the refractive power) of multifocal phase plate 112 may be such that the location of the first focus F1 and the second focus F2 along the optical axis 108 are configured to provide near vision and distant vision. That is, the first focus F1 is configured to provide distant vision, while the add power of the multifocal phase plate 112 is configured such that the second focus F2 provides near vision. For example, in typical embodiments a near vision add power is 3.0 or 4.0 Diopters. Alternatively, the add power may be such that the first focus F1 provides distant vision, while the second focus F2 provides intermediate vision. For example, F2 may typically be 1-2.5 D.

Ophthalmic lens 100 may be an IOL, such as IOL 20 of FIG. 1, for placement in either the posterior or anterior chambers of an eye. As such, ophthalmic lens 100 may be used to replace the natural lens of the eye, such as after removal of the natural lens during cataract surgery. Alternatively, ophthalmic lens 100 may be of any sort mentioned herein.

Foldable/deformable materials are particularly advantageous for formation of implantable ones of ophthalmic lens 100, in part because lenses made from such deformable materials may be rolled, folded or otherwise deformed and inserted into the eye through a small incision. The lens material preferably has a refractive index allowing a relatively thin, and preferably flexible, optic section including the phase plate. When ophthalmic lens 100 is an intraocular lens, optic 102 may have a diameter of about 4 mm or less to about 7 mm or more, by way of non-limiting example.

When configured as an IOL, ophthalmic lens 100 may comprise any of the various means available in the art for centering or otherwise disposing optic 102 on lens 100 within the eye. For example, ophthalmic lens 100 may comprise one or more fixation members or haptics. The haptics may be made of the same material as optic 102 and/or integrally formed therewith. Alternatively, one or more haptics may be formed separately and attached to optic 102. The haptics may comprise any of a variety of materials which exhibit sufficient supporting strength and resilience, and/or which are substantially biologically inert in an intended in-vivo environment. Suitable materials for this purpose include, for example, polymeric materials such as silicone polymeric materials, acrylic polymeric materials, hydrogel-forming polymeric materials, such as polyhydroxyethylmethacrylate, polyphosphazenes, polyurethanes, and mixtures thereof and the like. In other exemplary embodiments, ophthalmic lens 100 may include a positioning means that allows optic 102 to move along optical axis 108 in response to deformation of the capsular bag and/or in response to the ciliary muscles of the eye. (i.e. accommodating IOLs)

Referring again specifically to FIG. 3, a multifocal phase plate 112 may comprise a first plurality 128 of echelettes 130. A first region 110 may typically include a central diffraction region 134 that is surrounded by echelettes 130. In traditional diffractive IOLs, the central diffraction region 134, along with surrounding echelettes are annular and rotationally symmetric in form. Determination of an outer diameter of each echelette is generally a function of design wavelength and the desired focal length of the lens. Each of the echelettes 130 may typically have an area that is substantially the same as each of the remaining echelettes 130. In symmetrical embodiments of lens 100, echelettes 130 may be offset parallel to the optical axis 108 so as to form steps 138 between adjacent echelettes 130. The steps 138 may be selected to produce a predefined phase relationship between each of the echelettes 130.

The present invention provides a multifocal IOL having rotationally asymmetric diffractive echelettes, which may include at least partially non-annular and/or non-continuous diffractive structures. The rotationally asymmetric nature of a multifocal diffractive IOL in accordance with the present invention is such that the subjective discomfort resulting from halos and/or reduced contrast vision is minimized. As used herein, rotational symmetry is defined, with respect to a diffractive lens, as a constant step height around a particular circumference on a subject lens. As such, rotational asymmetry is herein defined as a nonconstant step height around a particular circumference along the optic or as a non-annular diffractive step about the optic. Rotationally asymmetry may also herein be defined as a step height that varies tangentially as a function of rotational angle.

Figure 4:
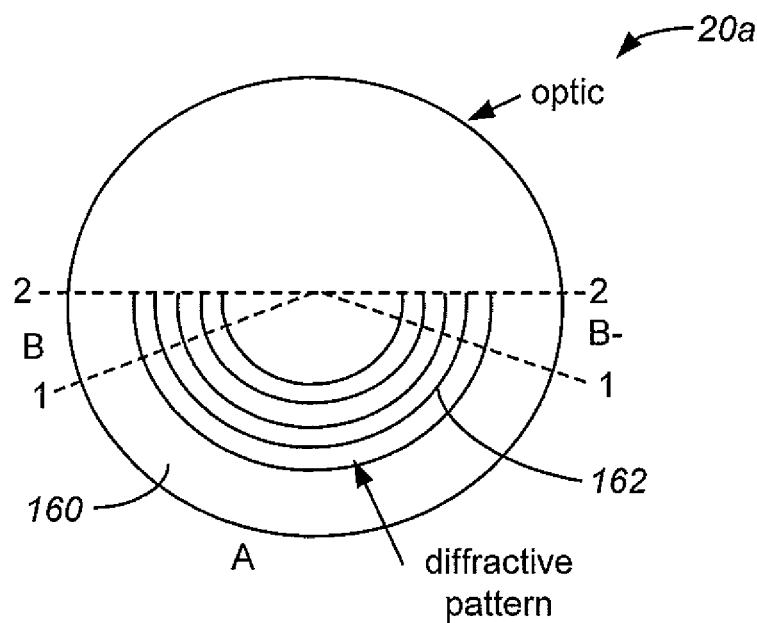
FIG. 4 is a schematic illustration of an ophthalmic lens according to embodiments of the present invention.

FIG. 4 is an illustration of a rotationally asymmetric multifocal diffractive IOL 20a in accordance with the present invention. Angular section A comprises a diffractive pattern 160, having a predetermined diffractive optical power, such as a power of about 2 to about 4 Diopters. The stepheight of the diffractive pattern establish a phase shift of about A. As a result, section A is monofocal. Angular section A is located towards the bottom of the optic and may cover between about 25% and about 45% of the optic. Angular sections B are multifocal diffractive transition sections 162, wherein the diffractive step height may change from a step height of section A to a zero diffractive step at the uppermost portion of section B. Angular section B is located adjacent and on both sides of Angular section A and may cover between about 5% to about 25% of the optic. In the illustration, angular section B may have a light distribution that varies between about 100 percent to near focus at positions labeled "1", and about 100 percent to far focus at positions labeled "2." Further, the uppermost portion of the illustrated optic, that is, that portion of the optic that is opposite section A along a diameter of the optic, may be a monofocal area, and more specifically a non-diffractive monofocal area. Section A may be spherical or aspherical.

The illustrated diffractive zones are asymmetric in that the semi-circular echelettes have a diffractive step height that varies. Additionally, only about half of the lens has diffractive echelettes, thus the diffractive structure is non-continuous. As illustrated herein, the upper portion covers about 50% of the optic, but in other embodiments, the upper portion may cover from about 33% to about 66%. Of course, as will be appreciated by those skilled in the pertinent arts in light of the discussion herein, the zones may alternatively be of any rotationally asymmetric configuration or otherwise variable diffractive power zones, and/or series of non-continuous, variable diffractive power zones.

Figure 5:
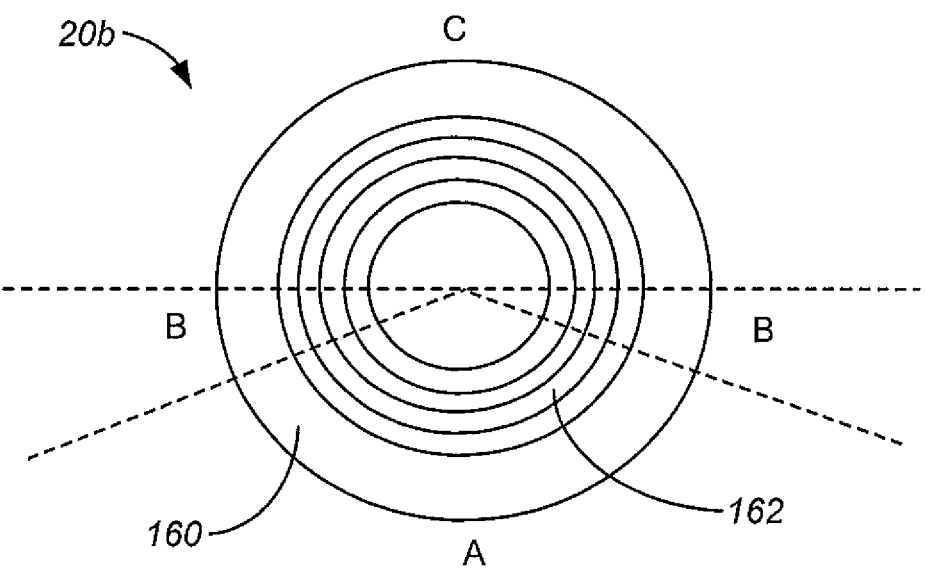
FIG. 5 is a schematic illustration of an ophthalmic lens according to embodiments of the present invention.

More particularly, FIG. 5 illustrates an alternative embodiment of a multifocal rotationally asymmetric IOL 20b, wherein the upper portion of the optic, i.e. that portion of the optic opposite section A along a diameter of the optic, includes a diffractive portion, labeled in FIG. 5 as section C. In the illustrated embodiment, section A may have a stepheight of the diffractive pattern with a phase shift of about 0.7λ. As a result, section A is bifocal, directing about 74 percent to near focus, and 14 percent to far focus, while about 12% of the light is directed in non-viewing orders. Section B may include transition zones (zones that transition from the stepheight of one adjacent zone and increases/decreases until it reaches the stepheight of the other adjacent zone), and section C may have a stepheight of the diffractive pattern with a phase shift of about 0.293μ. As a result, section C is a bifocal, directing about 13 percent of the light to near focus, and 75 percent to far focus, while about 12% of the light is directed to non-viewing orders. Thereby, the upper portion of the optic may be multifocal, diffractive, far-dominant, thus allowing further fine tuning to improve visual quality and to eliminate halos. Of note, as was the case in the illustrated embodiment of FIG. 4, the embodiment of FIG. 5 is rotationally asymmetric at least in that the diffractive phase delay, step height, i.e. the light distribution, changes with the meridian of the optic. Additionally, the percentage of the optic that each zone covers in FIG. 5 may be equivalent to the ranges disclosed in FIG. 4.

In another preferred embodiment, the upper portion of FIG. 5, section C, may be a diffractive monofocal, and sections A and B may be a diffractive bifocal with differing light distributions. Other variations include rotationally asymmetric diffractive structures which cover approximately 10% to 100% of the optic with light distributions between about 100% to near focus to about 100% to far focus. Additionally, the number of rotationally asymmetric angular sections may vary between 1 and 32 with the percentage of the optic that each section covers varying between 5% and 100%. Additionally, the light distribution may be varied versus the meridian by changing the diffractive echelette shape for different meridians, as is disclosed in application US2009/0268158. Additionally, the light distribution may be varied radially, for example, such as also disclosed in application Ser. Nos. 12/109,251 (Weeber), 11/000,770 (Simpson), and 11/259,524 (Bandhauer).

In another preferred embodiment disclosed in FIG. 6, a single ring microstructure 200 for extending depth of focus as detailed below may be added to the aforementioned rotationally asymmetric diffractive embodiments. Addition of the single ring microstructure to the rotationally asymmetric designs disclosed herein extends depth of focus without adding halos. In another preferred embodiment, a limited number of rings, or echelettes, as detailed below, may be added to extend depth of focus.

Of course, any of the examples detailed herein may be applied to any type of ophthalmic lenses, including spectacle lenses, contact lenses, corneal inlays or inlays, phakic lenses, and/or piggy-back lenses. Additionally, any of the examples detailed herein may be imposed on any base refractive profiles, e.g. spherical, aspheric, or toric.

Figure 6:
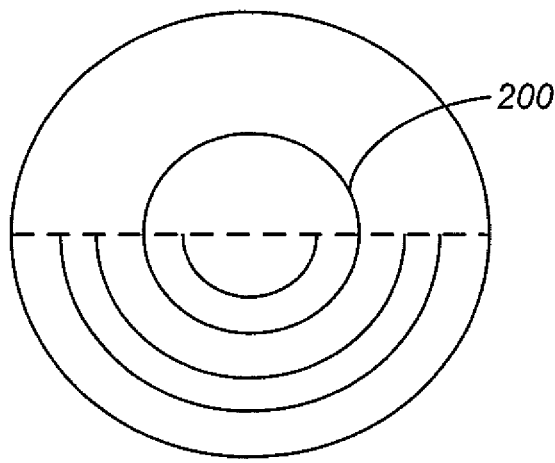
FIG. 6 is a schematic illustration of an ophthalmic lens according to embodiments of the present invention.

While certain zones in FIG. 4-6 show segments of constant phase delay, stepheight, or light distribution, it should be appreciated that in alternative embodiments, the phase delay, stepheight, or light distribution may vary smoothly over the entire circumference of the echelettes, as in FIG. 4, section B. Other exemplary embodiments include stepheights which transition abruptly.

Figure 7:
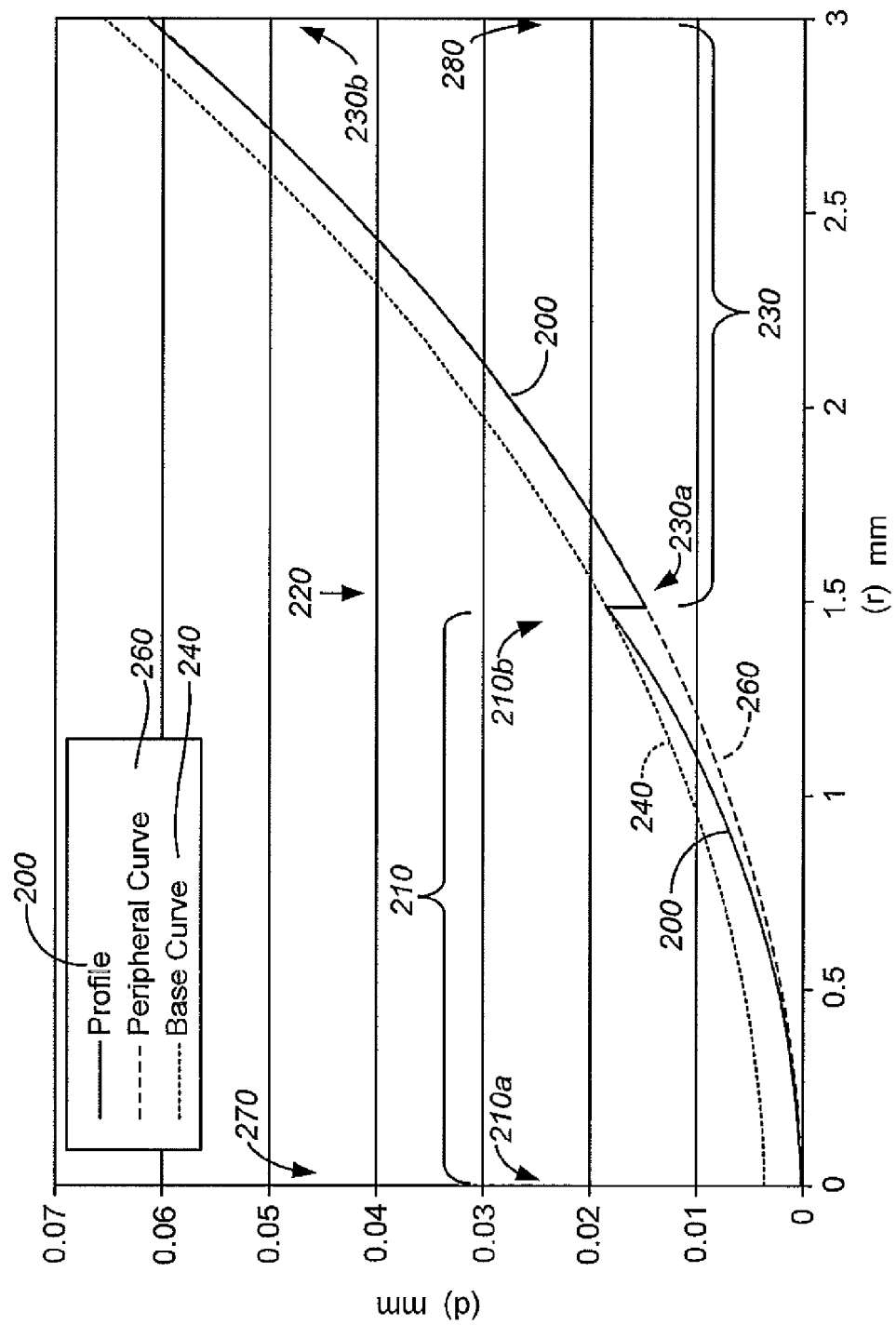
FIG. 7 shows aspects of a single microstructure lens according to embodiments of the present invention.

FIG. 7 discloses the single ring microstructure for extending depth of focus as detailed in U.S. Patent Application No. 61/288,255 filed on Dec. 18, 2009 and Single Microstructure Lens, Systems And Methods, U.S. patent application Ser. No. 12/971,506, filed concurrently herewith, both incorporated herein by reference. The single ring microstructure may be placed on the side opposing the rotationally asymmetric diffractive structure, or may be incorporated on the same side as seen in FIG. 6. In addition, the ring 200 may have a constant step height or may vary as detailed above.

Only half of the lens is shown in FIG. 7, although since the single ring microstructure is rotationally symmetric, the other half is a mirror image that complements the lens at the left side of FIG. 7. Profile 200 of the single ring surface includes an inner portion or single ring 210, a step or transition 220, and an outer portion 230. Inner portion 210 extends between a central location 270 of profile 200 and transition 220, and outer portion 230 extends between transition 220 and a peripheral location 280 of profile 200. Central location 270 is typically disposed at the optical axis. Transition 220 is disposed at a distance of about 1.5 mm from the optical axis, and peripheral location 280 is disposed at the diameter of the clear aperture of the lens, here at a distance of about 3.0 mm from the optical axis. In some cases, transition 220 can be disposed at a distance from the optical axis that is within a range from about 0.5 mm to about 2.0 mm, and peripheral location 280 can be disposed at a distance from the optical axis that is within a range from about 2.0 to about 3.5 mm, or bigger (for example, for contact lenses, the ranges would be scaled due to the larger sizes of the contact lens compared to an IOL).

As shown in FIG. 7, the surface height or sag (d) from a reference plane perpendicular to the optical axis, of each point on the lens profile is plotted against the radial distance (r) from the optical axis of the lens. As shown here, the value of displacement or total sag (d) can have a value within a range from about 0 mm to about 0.07 mm. The total sag can depend on the refractive shape of the surface and can have a value, for an IOL, of typically between 0 mm and about 2 mm, or to about minus 2 mm, in cases where the surface is concave.

Inner Portion

Inner portion or echelette 210 includes a center 210$a$ and a peripheral edge 210$b$. At center or central section 210$a$ of inner portion 210, the sag (d) of inner portion 210 is substantially equivalent to the displacement or sag (d) of peripheral curve 260. At peripheral edge 210$b$, the sag (d) of inner portion 210 is substantially equivalent to the sag (d) of diffractive base curve 240. Where radial distance (r) is zero, sag (d) of inner portion 210 is equivalent to the value of the peripheral curve 260. The value of sag (d) between radial distance zero and radial distance at the peripheral edge 210$b$, for example at 1.5 mm, gradually and smoothly changes from the value of peripheral curve 260 (at r=0) to diffractive base curve 240 (at r=1.5 mm) in a parabolic fashion. As shown here, inner portion 210 can present a parabolic shape, for example as described in Equation 4a of Cohen, Applied Optics, 31:19, pp. 3750-3754 (1992), incorporated herein by reference.

Transition

At the peripheral edge 210$b$, where the radial distance (r) is 1.5 mm, the value of sag (d) steps or changes from the value of diffractive base curve 240 to the value of peripheral curve 260. Where radial distance (r) corresponds to transition 220, sag (d) of inner portion 210 is equivalent to the value of the diffractive base curve 240. Relatedly, the displacement of the profile 200 approaches that of the peripheral curve 260 as the radial distance increases from a value of zero to a value of about 1.5 mm. The value of the offset can be determined along the vertical axis. The offset value may be selected depending on the amount of phase delay. According to one embodiment, the inner portion 210 and the outer portion 230 may not end up at the same vertical height at position 210$b$/230$a$. One way to connect these two endpoints is by using a straight vertical line. As shown here, the diffractive transition step provides a sharp step in the profile. In some cases the transition is characterized by a step height having a value within a range from about 0.5 microns and about 4 microns.

Outer Portion

Outer portion 230 includes an inner or central edge 230$a$ and a peripheral edge 230$b$. At inner edge 230$a$, the sag (d) of outer portion 230 is substantially equivalent to the sag (d) of peripheral curve 260. At peripheral edge 230$b$, the sag (d) of outer portion 230 remains substantially equivalent to the sag (d) of peripheral curve 260. The value of sag (d) for the outer portion 230 of profile 100 between radial distance 1.5 mm and radial distance 3.0 mm is equivalent to the value of peripheral curve 260. The sag of the profile 200 and the peripheral curve 260 are approximately equivalent between radial distance values of 1.5 mm and 3.0 mm.

The limited ring embodiments comprise of adding a limited number of echelettes to the above detailed single ring microstructure. In general such limited ring embodiments comprise of a limited number of echelettes that are either adjacent or non-adjacent to the inner central echelette and may or may not be separated by a refractive region. In some exemplary embodiments, every $2^{nd}$, $3^{rd}$, $4^{th}$, or $5^{th}$ echelette in Section A in FIGS. 4 and/or 5 may be extended into a full ring similar to ring 200 in FIG. 6. It should be appreciated that any variation of limited ring embodiments falls within the scope of this invention.

Figure 7A:
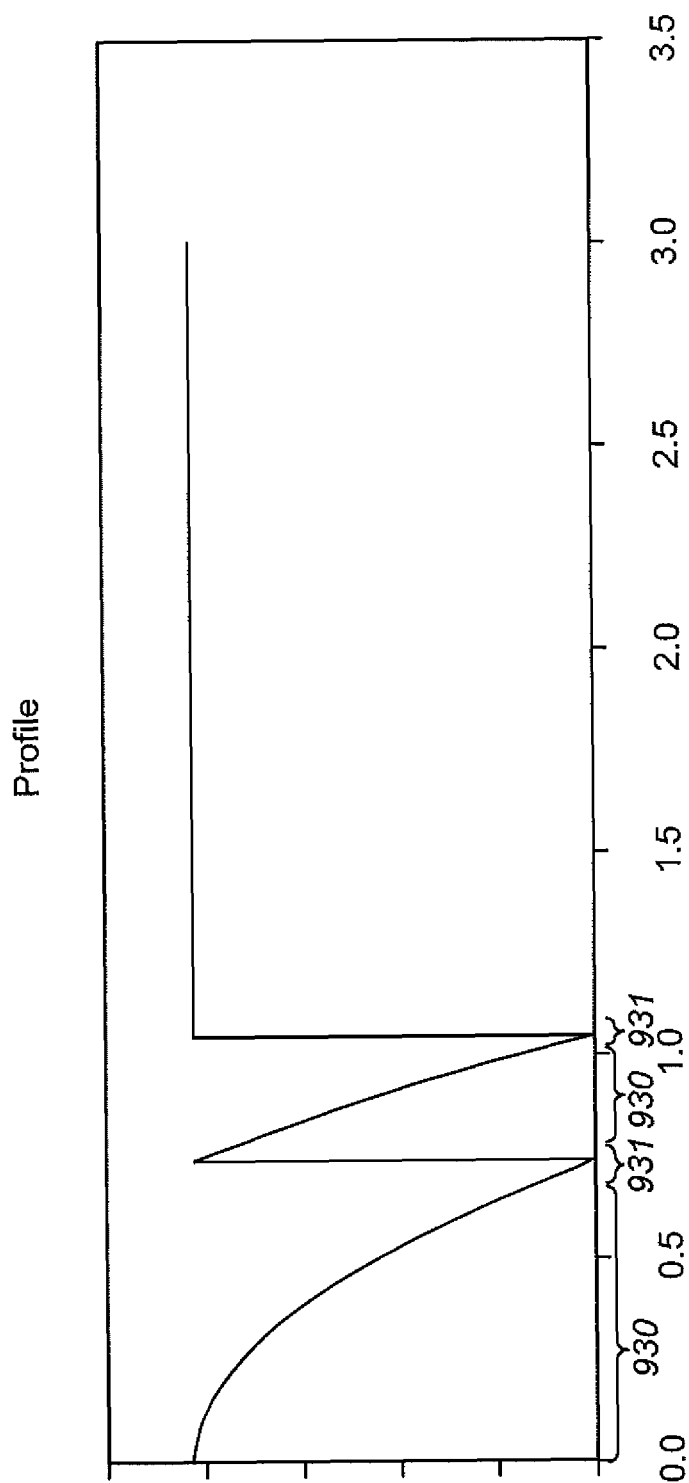
FIG. 7a illustrates aspects of a lens profile according to embodiments of the present invention.

FIG. 7A provides a graphical representation of a portion of a lens diffractive profile with a central echelette and one peripheral adjacent echelette according to embodiments of the present invention. In FIG. 7A, the height of the surface relief profile (from a plane perpendicular to the light rays) of each point on the echelettes surface is plotted against the distance from the optical axis of the lens. The echelettes can have a characteristic optical zone 930 and transition zone 931. Optical zone 930 can have a shape or downward slope that may be linear when plotted against p as shown in FIG. 7A. When plotted against radius r, optical zone 930 can have a shape or downward slope that is parabolic. Central and peripheral echelettes can have a surface area that is between 0.7 and 7 mm². For example, the echelettes may have a surface area that is 0.85 mm². An outer (refractive) zone can follow the base radius with a fixed offset. Exemplary embodiments include peripheral echelette(s) that are similar in shape (e.g. elliptical) and variable stepheight as the central echelette. Of course, this invention includes those embodiments where the peripheral echelette(s) differ in shape and/or variable stepheight as compared to the central echelette.

Figure 8:
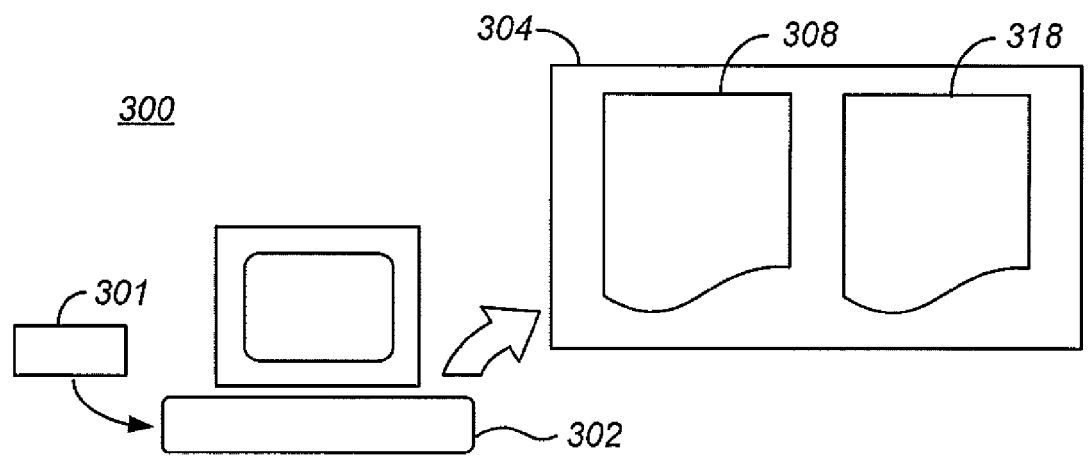
FIG. 8 is a block diagram illustrating a clinical computing system.

FIG. 8 is a block diagram illustrating the implementation of the present invention, as set forth hereinabove, in a clinical system 300 comprised of one or more apparatuses that of capable of assessing the eye's biometry and of performing the calculations and comparisons set forth in designing the asymmetric diffractive multifocal elements discussed herein. The system 300 may include a biometric reader and/or input 301, a processor 302, and a computer readable memory 304 coupled to the processor 302. The computer readable memory 304 includes therein an array of ordered values 308 and sequences of instructions 318 which, when executed by the processor 302, cause the processor 302 to select and/or design the diffractive structures and manufacture the lens through, for example, known molding or lathe techniques. The array of ordered values 308 may comprise data used or obtained from and for use in design methods consistent with embodiments of the invention. For example, the array of ordered values 308 may comprise one or more desired refractive outcomes, parameters of an eye model based on one or more characteristics of at least one eye, and/or data related to an IOL, a set of IOLs, and one or more rotationally asymmetric echelettes.

The sequence of instructions 318 may include one or more steps consistent with embodiments of the invention. In some embodiments, the sequence of instructions 318 may include application of calculations, algorithms, customization, simulation, comparison, remote communications and networking, and the like.

The processor 302 may be embodied in a general purpose desktop or laptop computer, and/or may comprise hardware and/or software associated with inputs 301. In certain embodiments, the system 300 may be configured to be electronically coupled to another device, such as one or more instruments for obtaining measurements of an eye or a plurality of eyes. Alternatively, the system 300 may be embodied in a handheld device that may be adapted to be electronically and/or wirelessly coupled to one or more other devices.

Although the invention has been described and pictured in an exemplary form with a certain degree of particularity, it should be understood that the present disclosure of the exemplary form has been made by way of example, and that numerous changes in the details of construction and combination and arrangement of parts and steps may be made without departing from the spirit and scope of the invention as set forth in the claims hereinafter.

What is claimed is:

1. An ophthalmic lens, comprising:
   an anterior face and a posterior face, the faces disposed about an optical axis;
   at least one diffractive region imposed on the anterior face or the posterior face, comprising a plurality of diffractive echelettes with stepheights that cause a phase delay, wherein the stepheights of each echelette vary tangentially as a function of rotational angle and wherein the phase delay varies tangentially as a function of rotational angle.

2. The ophthalmic lens of claim 1, wherein the diffractive region is located within an angular section of the optic.

3. The ophthalmic lens of claim 1, wherein the diffractive region is within an angular section that covers between 5 and 66% of the optic.

4. The ophthalmic lens of claim 3, wherein the stepheights within an angular section of an optic, transition from the stepheight of one adjacent zone to the stepheight of another adjacent zone.

5. The ophthalmic lens of claim 3, wherein the stepheights Within an angular section of an optic, transition from the stepheight of one diffractive zone to the stepheight of an adjacent monofocal zone.

6. The ophthalmic lens of claim 3, wherein the stepheights within an angular section of an optic, transition from the stepheight of one diffractive zone to another adjacent refractive zone.

7. An ophthalmic lens, comprising:
   an optic having an anterior surface, a posterior surface, and an optical axis, the optic comprising:
      at least one refractive region associated with at least one of the anterior surface and the posterior surface; and
      at least one diffractive region comprising a plurality of diffractive echelettes, each echelette having a rotational asymmetry with respect to the optical axis, the diffractive region having at least two diffractive orders with associated diffractive optical powers configured for forming, in conjunction with the at least one refractive region, at least a first focus and a second focus.

8. The ophthalmic lens of claim 7, wherein the refractive region comprises from about 33% to about 66% of the optic.

9. The ophthalmic lens of claim 7, wherein light at a design wavelength that is incident on the ophthalmic lens is split between the zeroeth diffraction order and the first diffraction order to form the first focus and the second focus.

10. The ophthalmic lens of claim 7, wherein each echelette comprises a step height that varies rotationally as a function of the rotational angle.

11. The ophthalmic lens of claim 7, wherein the plurality of diffractive echelettes comprises:
    a first section comprising a monofocal diffractive pattern having a first one of the associated diffractive optical powers; and
    a second section comprising a plurality of multifocal transitions.

12. The ophthalmic lens of claim 11, wherein the plurality of multifocal transitions comprise a transition from about 100 percent to the first focus to about 100 percent to the second focus.

13. The ophthalmic lens of claim 11, wherein the plurality of diffractive echelettes further comprises a third region comprising a variable focus between the first focus and the second focus.

14. The ophthalmic lens of claim 13, wherein the variable focus comprises about 25 percent to the first focus comprising a near focus, and about 75 percent to the second focus comprising a distant focus.

* * * * *